(12) United States Patent
Sun et al.

(10) Patent No.: US 11,421,272 B2
(45) Date of Patent: Aug. 23, 2022

(54) POSITIONING METHOD, POSITIONING APPARATUS AND SEQUENCING SYSTEM

(71) Applicant: GeneMind Biosciences Company Limited, Guangdong (CN)

(72) Inventors: Ruitao Sun, Guangdong (CN); Songzhen Zhang, Guangdong (CN); Zefei Jiang, Guangdong (CN); Zhiliang Zhou, Guangdong (CN); Qin Yan, Guangdong (CN)

(73) Assignee: GeneMind Biosciences Company Limited, Shenzhen (CN)

( * ) Notice: Subject to any disclaimer, the term of this patent is extended or adjusted under 35 U.S.C. 154(b) by 0 days.

(21) Appl. No.: 17/417,035

(22) PCT Filed: Sep. 29, 2019

(86) PCT No.: PCT/CN2019/109046
§ 371 (c)(1),
(2) Date: Jun. 21, 2021

(87) PCT Pub. No.: WO2020/134289
PCT Pub. Date: Jul. 2, 2020

(65) Prior Publication Data
US 2022/0090190 A1    Mar. 24, 2022

(30) Foreign Application Priority Data

Dec. 26, 2018 (CN) .......................... 201811600287.6
Dec. 29, 2018 (CN) .......................... 201811634436.0

(51) Int. Cl.
*C12Q 1/6869* (2018.01)
*G01N 21/01* (2006.01)
(Continued)

(52) U.S. Cl.
CPC ............. *C12Q 1/6869* (2013.01); *B01J 19/18* (2013.01); *G01N 21/01* (2013.01); *G02B 21/26* (2013.01);
(Continued)

(58) Field of Classification Search
CPC ....... C12Q 1/6869; B01J 19/18; G01N 21/01; G01N 2035/00237; G02B 21/26; G03B 5/00
See application file for complete search history.

(56) References Cited

U.S. PATENT DOCUMENTS

2004/0047033 A1   3/2004  Nakagawa
2014/0152888 A1*  6/2014  Staker ................. G02B 27/646
                                            348/373
(Continued)

FOREIGN PATENT DOCUMENTS

CN     101369523 A    2/2009
CN     102692347 A    9/2012
(Continued)

OTHER PUBLICATIONS

International Search Report and Written Opinion of International Application PCT/CN2019/109046, dated Dec. 31, 2019, (8 pages).
(Continued)

*Primary Examiner* — Jill A Warden
*Assistant Examiner* — John McGuirk
(74) *Attorney, Agent, or Firm* — Seed IP Law Group LLP (57) ABSTRACT

Disclosed are a positioning method, a positioning apparatus and a sequencing system (300). The sequencing system (300) comprises an imaging assembly (110) and a mobile platform (102), wherein the imaging assembly (110) comprises an optical axis (OP), the mobile platform (102) bears a reaction apparatus (200), the stroke of the mobile platform (102) in a first direction is controlled by means of a limiting
(Continued)

switch, and the stroke comprises a first limit. The method comprises the steps: (a) moving, by a first step distance, the mobile platform (102) in a direction approaching the first limit, until the distance between a current position of the reaction apparatus (200) and the previous position of the reaction apparatus (200) is less than the first step distance; (b) moving the mobile platform (102) in a direction that is the opposite of the moving direction in step (a); (c) moving the mobile platform (102) in the moving direction in step (a), until the mobile platform (102) reaches the first limit; and (d) moving, by a preset distance, the mobile platform (102) in the direction that is the opposite of the moving direction in step (a), so that the positions of the optical axis (OP) and the reaction apparatus (200) satisfy a preset relationship. According to the method, the quick and precise positioning of the mobile platform (102) can be realized by means of moving back and forth in the first direction, such that the positions of the optical axis (OP) and the reaction apparatus (200) satisfy a preset relationship.

20 Claims, 4 Drawing Sheets

(51) Int. Cl.
    *G02B 21/26*     (2006.01)
    *G03B 5/00*     (2021.01)
    *B01J 19/18*     (2006.01)
    *G01N 35/00*     (2006.01)

(52) U.S. Cl.
    CPC ..... *G03B 5/00* (2013.01); *G01N 2035/00237* (2013.01)

(56) References Cited

U.S. PATENT DOCUMENTS

| | | | |
|---|---|---|---|
| 2014/0267669 A1* | 9/2014 | Stoops | G06T 7/73 |
| | | | 348/79 |
| 2018/0252936 A1* | 9/2018 | Owens | G01N 21/6456 |

FOREIGN PATENT DOCUMENTS

| | | |
|---|---|---|
| CN | 104364697 A | 2/2015 |
| CN | 104900558 A | 9/2015 |
| CN | 204999894 U | 1/2016 |
| CN | 105474236 A | 4/2016 |

OTHER PUBLICATIONS

Nakamura et al., "High-Speed Positioning of a Linear Stage Using Feedback Error Learning Control: Improvement of Learning Time and Accuracy," *IEEE International Conference on Industrial Technology*, Athens, Greece, Mar. 19-21, 2012, pp. 1079-1085. https://doi.org/10.1109/ICIT.2012.6210083.

Shiou et al., "Development of a real-time closed-loop micro-/nano-positioning system embedded with a capacitive sensor," *Measurement Science and Technology*, 21(5):1-10, Mar. 23, 2010. https://doi.org/10.1088/0957-0233/21/5/054007.

\* cited by examiner

POSITIONING METHOD, POSITIONING APPARATUS AND SEQUENCING SYSTEM

TECHNICAL FIELD

The present disclosure relates to the field of positioning, in particular to a positioning method, a positioning device and a sequencing system.

BACKGROUND

With the continuous development of nucleic acid sequencing technologies, sequencing systems are also continuously updated. For a sequencing system/platform that detects nucleic acid molecules to be detected in a reactor based on an optical imaging system, the sequencing system comprises an imaging assembly for continuously photographing nucleic acid molecules in a reactor (e.g., flowcell) during a sequencing reaction, and the photographed images are analyzed to give a sequencing result.

In automated nucleic acid sequencing, it is desirable to ensure that the imaging assembly is able to acquire information about the target field of view through photographing, and continuously acquire information of all target fields of view in a predetermined range in one circle of sequencing reaction or one sequencing reaction, and at the beginning, automatic and accurate adjustment and determination of the relative positions of the imaging assembly and the reactor is very important. Therefore, it is necessary to provide a positioning method.

SUMMARY

Therefore, embodiments of the present disclosure provide a positioning method, a positioning device and a sequencing system.

An embodiment of the present disclosure provides a positioning method for a sequencing system, wherein the sequencing system comprises an imaging assembly and a mobile platform, the imaging assembly comprises an optical axis, the mobile platform bears a reaction device, the imaging assembly is located above the reaction device, a limit switch is configured for controlling stroke of the mobile platform in a first direction, and the stroke comprises a first limit, the method comprising:

(a) moving the mobile platform in a direction approaching the first limit at a first step space until a distance between a current position of the reaction device and a previous position of the reaction device is smaller than the first step space;

(b) moving the mobile platform in a direction opposite to the moving direction in (a);

(c) moving the mobile platform in the moving direction in (a) until the mobile platform reaches the first limit; and (d) moving the mobile platform in the direction opposite to the moving direction in (a) for a preset distance such that the optical axis and the position of the reaction device satisfy a preset relationship.

The positioning method described above comprises setting a moving speed/a moving step space, and by moving the mobile platform back and forth in the first direction, rapid and precise positioning can be realized, such that the optical axis of the imaging assembly and the position of the reaction device satisfy the preset relationship, and thereby subsequently the imaging assembly can continuously photograph to give information of all target fields of view in a predetermined area.

The positioning method is suitable for various sequencing platforms based on optical detection, including but not limited to HiSeq/MiSeq/NextSeq/NovaSeq of Illumina, BGISEQ50/500 of BGI, Sequel of PacBio, etc.

A sequencing system according to an embodiment of the present disclosure comprises a positioning device, an imaging assembly and a mobile platform, wherein the imaging assembly comprises an optical axis, the mobile platform bears a reaction device, the imaging assembly is located above the reaction device, a limit switch is configured for controlling stroke of the mobile platform in a first direction, the stroke comprises a first limit, and the positioning device is configured for:

(a) moving the mobile platform in a direction approaching the first limit at a first step space until a distance between a current position of the reaction device and a previous position of the reaction device is smaller than the first step space;

(b) moving the mobile platform in a direction away from the first limit;

(c) moving the mobile platform in a direction approaching the first limit until the mobile platform reaches the first limit; and (d) moving the mobile platform in the direction away from the first limit for a preset distance such that the optical axis and the position of the reaction device satisfy a preset relationship.

An embodiment of the present disclosure provides a positioning device for a sequencing system, wherein the sequencing system comprises an imaging assembly and a mobile platform, the imaging assembly comprises an optical axis, the mobile platform bears a reaction device, the imaging assembly is located above the reaction device, a limit switch is configured for controlling stroke of the mobile platform in a first direction, and the stroke comprises a first limit, the positioning device comprising:

a storage device configured for storing data, wherein the data comprises a computer-executable program; and a processor configured for executing the computer-executable program, wherein executing the computer-executable program comprises performing the steps of the positioning method described above.

The sequencing system according to an embodiment of the present disclosure comprises the positioning device described above.

The additional aspects and advantages of the embodiments of the present disclosure will be partially set forth in the following description, and will partially become apparent from the following description or be appreciated by practice of the embodiments of the present disclosure.

BRIEF DESCRIPTION OF THE DRAWINGS

The aforementioned and/or additional aspects and advantages of embodiments of the present disclosure will become apparent and easily understood from the description of the embodiments in reference to the following drawings, among which.

DETAILED DESCRIPTION

The embodiments of the present disclosure are described in detail below, and the examples of the embodiments are shown in the accompanying drawings, throughout which identical or similar reference numerals represent identical or similar elements or elements having identical or similar functions. The embodiments described below by reference to the accompanying drawings are exemplary and are merely intended to explain the present disclosure rather than be construed as limiting the present disclosure.

In the description of the present disclosure, the terms "first" and "second" are used for description purpose only rather than construed as indicating or implying relative importance or implicitly indicating the number of indicated technical features. Therefore, features defined with "first" and "second" may explicitly or implicitly include one or more of the features. In the description of the present disclosure, unless otherwise specifically defined, "a plurality of" means two or more than two.

In the description of the present disclosure, it should be noted that unless otherwise clearly specified and defined, "connect" should be comprehended in its broad sense. For example, "connect" may be "fixedly connect", "detachably connect" or "integrally connect"; "mechanically connect", "electrically connect" or "communicate with each other"; or "directly interconnect", "indirectly interconnect through an intermediate", "the communication between the interiors of two elements" or "the interaction between two elements". For those of ordinary skill in the art, the specific meanings of the aforementioned terms in the present disclosure can be understood according to specific conditions.

The following disclosure provides many different embodiments or examples for implementing different structures of the present disclosure. To simplify the disclosure of the present disclosure, components and settings of certain examples are described below. In addition, the present disclosure may repeat reference numbers and/or reference letters in different examples. Such repetition is intended for simplicity and clarity rather than for indicating the relationship between various embodiments and/or settings discussed.

The "sequence determination" refers to nucleic acid sequence determination, also known as sequencing, including DNA sequencing and/or RNA sequencing, and/or including long fragment sequencing and/or short fragment sequencing. The "sequence determination reaction" refers to sequencing reaction.

Figure 1:
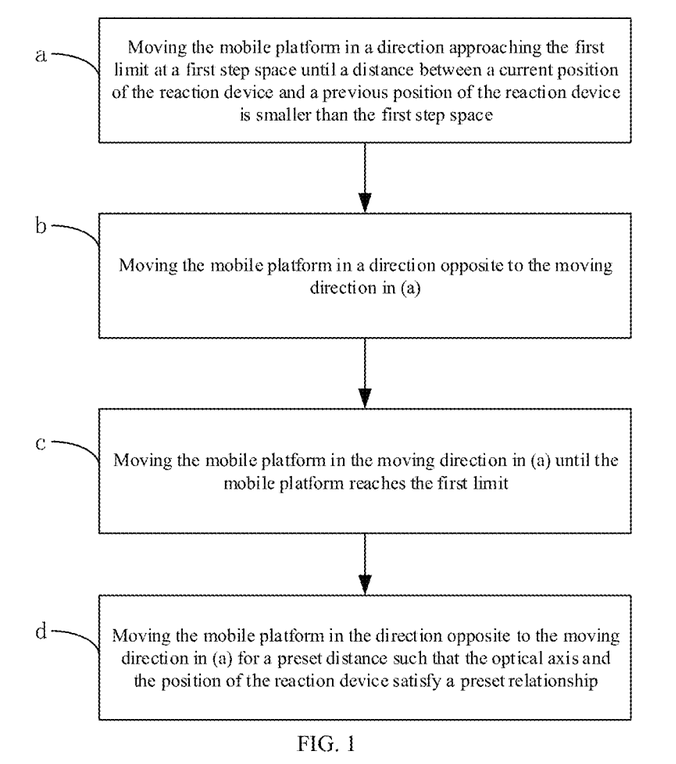
FIG. 1 is a flowchart of a positioning method according to an embodiment of the present disclosure.
Figure 2:
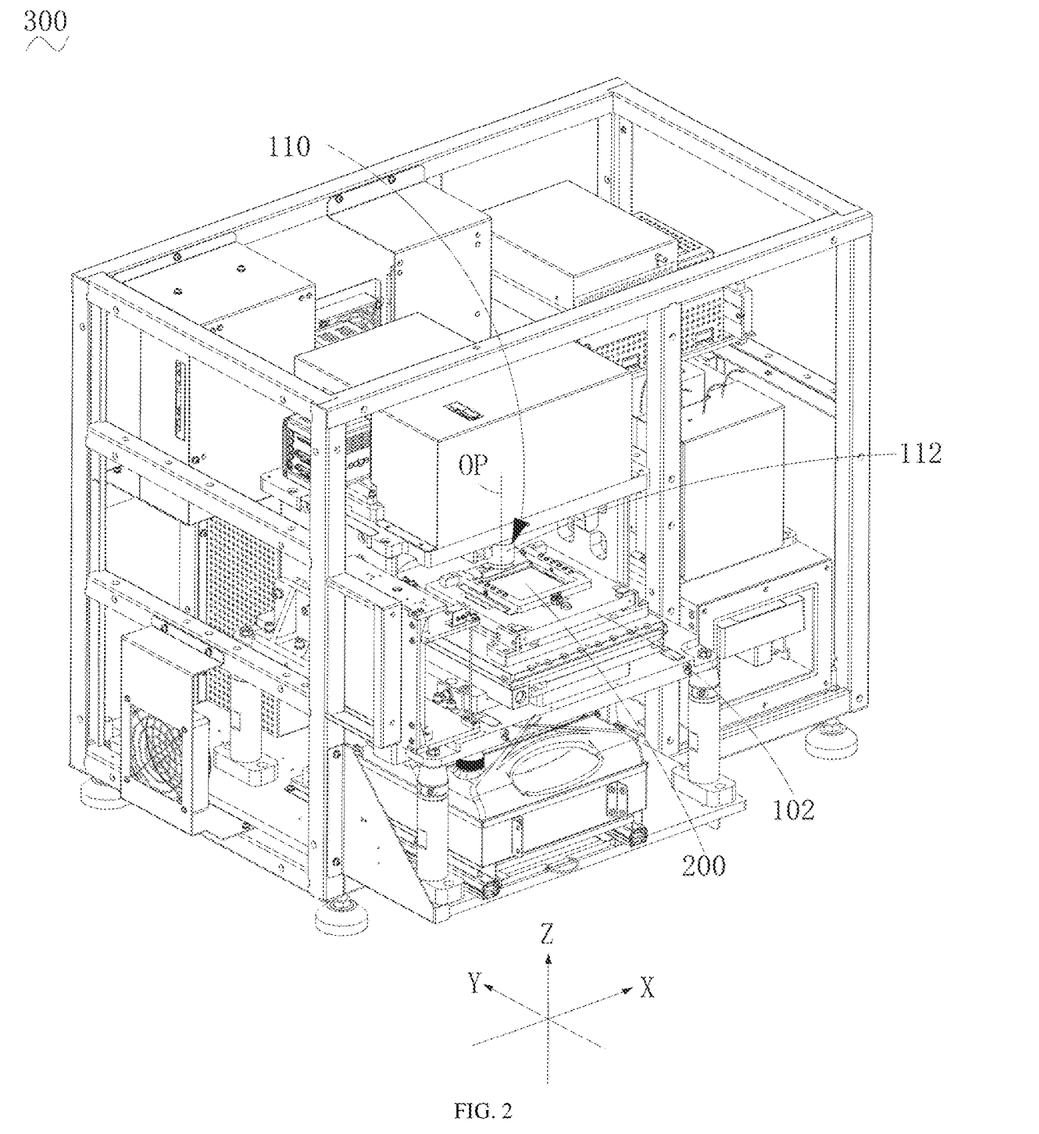
FIG. 2 is a structural schematic diagram of a sequencing system according to an embodiment of the present disclosure.

Referring to FIG. 1, an embodiment of the present disclosure provides a positioning method for an sequencing system 300. Referring to FIG. 2, the sequencing system 300 comprises an imaging assembly 110 and a mobile platform 102; the imaging assembly 110 comprises an optical axis OP, and the mobile platform 102 bears a reaction device 200; the imaging assembly 110 is located above the reaction device 200, a limit switch is configured for controlling stroke of the mobile platform 102 in a first direction, and the stroke comprises a first limit; the method comprises:

(a) moving the mobile platform 102 in a direction approaching the first limit at a first step space until a distance between a current position of the reaction device 200 and a previous position of the reaction device 200 is smaller than the first step space;

(b) moving the mobile platform 102 in a direction opposite to the moving direction in (a);

(c) moving the mobile platform 102 in the moving direction in (a) until the mobile platform 102 reaches the first limit; and (d) moving the mobile platform 102 in the direction opposite to the moving direction in (a) for a preset distance such that the optical axis OP and the position of the reaction device 200 satisfy a preset relationship.

The positioning method described above comprises setting a moving speed/a moving step space, and by moving the mobile platform back and forth in the first direction, rapid and precise positioning can be realized, such that the optical axis of the imaging assembly 110 and the position of the reaction device 200 satisfy the preset relationship, and thereby subsequently the imaging assembly 110 can continuously photograph to give information of all target fields of view in a predetermined area.

Specifically, referring to FIG. 2, in some examples, the reaction device 200 can be fixedly placed on the mobile platform 102, and the sequencing system 300 can introduce a reaction reagent/solution into the reaction device 200. The reaction device 200 is provided with one or more channels. The reaction reagent/solution is in the channel 200, and nucleic acid molecules are in the reaction reagent/solution. Imaging assembly 110 is arranged above the reaction device 200, such that images of nucleic acid molecules with an optically detectable label in a specific position (field of view) of the reaction device 200 can be acquired during the sequencing of nucleic acid molecules, wherein the optically detectable label is, e.g., a fluorescent molecule. The reaction device 200 is, e.g., a flowcell.

In some embodiments, the imaging assembly 110 comprises an automatic focusing module. When the automatic focusing module is used for focusing on a specific position of the reaction device, the imaging assembly 110 is stationary, and mobile platform 102 drives the reaction device 200 to move in a plane perpendicular to the optical axis OP according to the information/instruction of the automatic focusing module, such that the imaging assembly 110 is able to acquire images of different positions of reaction device 200. Generally, the sequencing system 300 comprises a limit switch, a driving module (such as a step motor) and an inquiry board card to control the movement of the mobile platform 102 and give coordinate values of the mobile platform 102 or the reaction device 200. The step motor drives the mobile platform to move, and the inquiry board card outputs real-time coordinate values of the reaction device 200/mobile platform 102 according to the number of steps of the movement of the step motor. The limit switch is configured for limiting the extreme movement position of the mobile platform 102. Due to the relatively fixed positions of the mobile platform 102 and the reaction device 200, the limit switch can also limit the extreme movement position of the reaction device 200. In another embodiment, the sequencing system 300 further comprises a mechanical stopper, which is arranged at one end of the stroke in the first direction approaching the limit switch and is configured for limiting the movement of the mobile platform 102.

Figure 3:
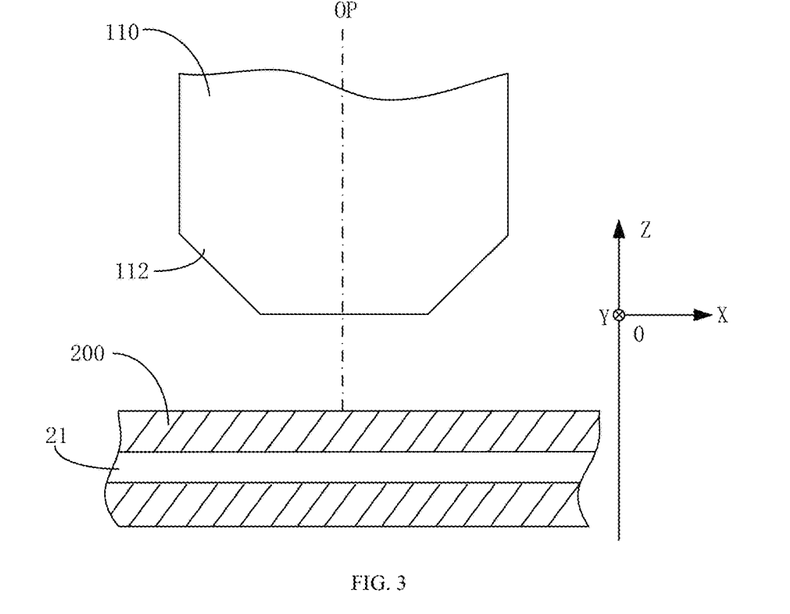
FIG. 3 is a structural schematic diagram of a portion of a sequencing system according to an embodiment of the present disclosure.

When the optical axis OP and the position of the reaction device 200 satisfy a preset relationship, the sequencing system 300, in the photographing stage, can control the imaging assembly 110 to photograph the reaction device 200 so as to give fluorescence images of the nucleic acid molecules. The imaging assembly 110 may comprise a microscope and a camera that acquires light from the microscope. Referring to the coordinate system shown in FIG. 3, before the positioning starts or at the start of the positioning, a lens (e.g., an objective lens 112 of the microscope) of the imaging assembly 110 is moved to a 0 point position of Z-axis, such as any position that is away from the reaction device 200 by certain distance in the Z-axis direction and is relatively in the middle of the X-axis direction, to prevent the objective lens 112 from colliding with the reaction device 200 below and the structures on both sides. The first direction is a direction along the Y-axis.

tively fast speed, although it is beneficial for fast positioning, there may also be great deviation in positioning due to larger inertia.

Figure 5:
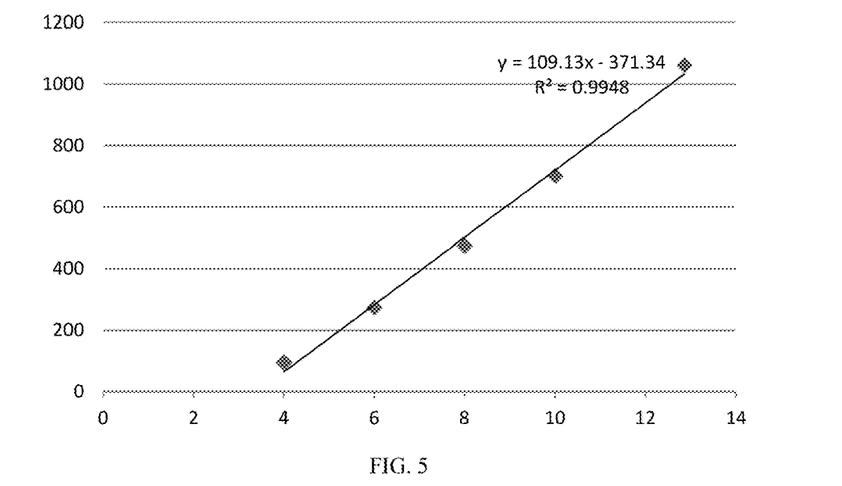
FIG. 5 is a schematic diagram showing the relationship between moving speed and deviation of a mobile platform according to an embodiment of the present disclosure.

In one example, according to multiple tests, as shown in Table 1, when the mobile platform 102 is set to reach the first limit at speeds V=12.8 mm/s and V=2 mm/s, the deviation between the two coordinates (Y-axis coordinates) of the first limits can reach 1000 μm. Table 1, based on the tests performed by the inventors, shows the difference between the coordinate values of the reaction device 200 (or the mobile platform 102) obtained when reaching the same position (for example, the first limit) at different speeds. FIG. 5 is a curve fitted according to the data in Table 1. The abscissa represents the speed, and the ordinate represents the difference value between the average coordinate value and the average coordinate value when the speed is 2 mm/s. It can be seen that the speed and the difference value (or average coordinate value of multiple measurements) satisfies the linear relationship.

TABLE 1

| Unit of speed mm/s Speed | Coordinate value 1 | Coordinate value 2 | Coordinate value 3 | Average value | Unit of coordinate value μm Difference value between the average value and that when the speed is 2 mm/s |
|---|---|---|---|---|---|
| 12.864 | 46292 | 46339 | 46319 | 46317 | 1061 |
| 10 | 45958 | 45943 | 45966 | 45956 | 700 |
| 8 | 45723 | 45722 | 45744 | 45730 | 474 |
| 6 | 45532 | 45534 | 45521 | 45529 | 273 |
| 4 | 45353 | 45341 | 45359 | 45351 | 95 |
| 2 | 45258 | 45263 | 45246 | 45256 | 0 |

Figure 4:
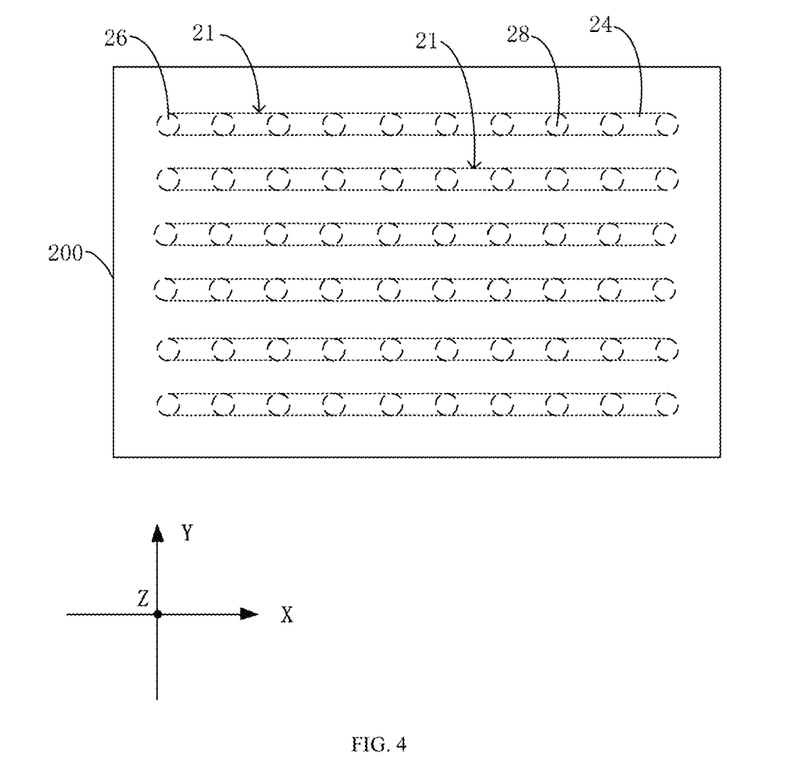
FIG. 4 is a structural schematic diagram of a reaction device according to an embodiment of the present disclosure.

In some embodiments, the reaction device 200 is provided with a plurality of channels 21, as shown in FIG. 4. Generally, any position of the first channel can be selected as the photographing start position, and the first channel can be set as required. For example, the first channel and/or the second channel in FIG. 4 can be set as the first channel By using the positioning method of the present embodiment, the optical axis OP of the imaging assembly 110 can be made to be perpendicular to the first channel, and if required, then the mobile platform 102 can be moved in the direction of X-axis such that the optical axis OP of the imaging assembly 110 is perpendicular to a specific position of the first channel so as to photograph and acquire images of the specific position (field of view). For example, from top to bottom in FIG. 4, the optical axis OP of the imaging assembly 110 is made to be perpendicular to a left end point 26 of the first channel 24 to start photographing.

The type of limit switch used is not limited by the present application, and the limit switch can be inductive (such as a photoelectric or electromagnetic limit switch), a contact-type limit switch, or a combination of various limit switches. In one example, the limit switch is an electromagnetic limit switch, and the mobile platform 102 is provided with a magnetic element. When the electromagnetic limit switch senses the magnetic element, the limit switch experiences a contact action to realize circuit switching and disconnection of the power supply of the driving module, so that the mobile platform 102 can be considered to reach a first limit in a first direction. Generally, since the limit switch is of specific precision, that is, the limit switch can sense the magnetic element within a certain distance range and respond, a position range is detected; moreover, when the driving module drives the mobile platform 102 to move at a rela- The moving speed in step (a) is not limited. Preferably, in some examples, in order to position quickly, in step (a), the mobile platform 102 can be set to move at a faster moving speed, and the first step space can be set/selected arbitrarily within a range less than the allowable stroke range of the mobile platform 102. In some examples, the allowable stroke range of the mobile platform 102 is about 15 cm, the first step space of the mobile platform 102 is less than 15 cm, and the first step space can be set to 10 cm, 8 cm, 5 cm, 3 cm, 2 cm, 1 cm, etc. In one example, the moving speed of the mobile platform 102 (V1) is 12.8 mm/s, and the first step space (Space1) is 2800 μm, which is the space between two adjacent channels.

When the distance between the current position P2 of the reaction device 200 and the previous position P1 of the reaction device 200 is smaller than the first step space, that is, when P2−P1<Space 1, that is, when the mobile platform 102 has not completed the step space, the limit switch is triggered to turn on so as to stop the movement of the mobile platform 102.

The moving speed of the mobile platform 102 in step (b) is not limited. In some examples, setting the moving direction in step (b) to be opposite to the moving direction in step (a) is to eliminate or reduce the influence of the moving speed in step (a) and detection precision of the limit switch on positioning. A minimum distance the mobile platform 102 needs to move in step (b) is related to the moving speed of the mobile platform 102 in step (a). Generally, the moving distance in step (b) is smaller compared to that in step (a). In step (b), a moving speed less than that in step (a) can be adopted. For example, the moving speed in step (a) is 12.8 mm/s, and the moving speed in step (b) can be set to be less than 12 mm/s, such as 10 mm/s, 8 mm/s, 6 mm/s, 4 mm/s or 2 mm/s.

Specifically, after the completion of step (a), a deviation is present between the coordinate values of the mobile platform 102 (or the reaction device 200) that are fed back and the actual position of the mobile platform 102 due to such reasons as the influence of the detection accuracy of the limit switch and the moving speed of the mobile platform 102. The actual position of the mobile platform 102 may exceed or fail to reach the coordinate position. Therefore, the step (b) is performed, in which the mobile platform 102 is moved in a direction opposite to the moving direction in step (a) for a certain distance, which can eliminate or reduce the positioning deviation caused by the moving speed of the mobile platform 102 in step (a). Generally, in step (a), the faster the moving speed of the mobile platform 102 is, the greater the inertia is and thereby the greater the resulting positioning deviation will be. Accordingly, in step (b), the distance of moving the mobile platform 102 in the direction opposite to the moving direction in step (a) can be set to a larger value. In one example, the positioning deviation caused by the moving speed in step (a) is about 800 μm, and the moving distance of the mobile platform 102 in step (b) can be set to be no less than 800 μm. For example, the moving distance in step (b) is set to 1000 μm, 1200 μm, 1500 μm, 2000 μm, or the like.

In some examples, the moving speed of the mobile platform 102 in step (c) is not greater than a first preset value, and the first preset value is related to an allowable error of positioning. Specifically, the reason of setting the first preset value is to allow the deviation between the actual position of the mobile platform 102 and the coordinate position is within an allowable error range of the positioning when the first limit is reached. The allowable error of the positioning is the space between the target positions in the moving direction. In one example, the allowable error of the positioning is the width of a channel 24, the length of the channel in the first direction (moving direction) is defined as the width of a channel 21, and the width of the channel 24 is 1.8 mm; based on the relationship between moving speed and deviation shown in FIG. 5, the first preset value can be set to 11.6 mm/s.

Specifically, in one example, it is desired to eliminate the position deviation caused by the moving speed of the mobile platform 102 in step (a) and/or step (b) by controlling the moving speed of the mobile platform 102 in step (c). The first preset value may be less than or equal to the moving speed of the mobile platform 102 in step (a). In one example, the error due to mechanical movement is allowed to be ±0.7 mm in positioning. The first preset value can be set to 9.8 mm/s.

In some examples, preferably, in step (c), the mobile platform 102 can be moved at a relatively low speed, such as at a moving speed less than 5 mm/s, 3 mm/s, etc., so that the deviation caused by this step is not greater than one-eighth, one-tenth, one-fifteenth, etc. of the allowable error of the positioning, and the error is basically negligible. Thus, in step (d), the mobile platform can be moved at a relatively fast speed and can reach the target position within the allowable error range of the positioning. In one example, the allowable error of the positioning is the width of the channel 24, and the width of the channel 24 is 1.8 mm; the mechanical tolerance caused by the reaction device 200, the mobile platform 102 and the mechanical connection positioning structure is about ±0.2 mm, and the error due to mechanical movement is allowed to be ±0.7 mm in positioning.

In certain embodiments, the moving speed of the mobile platform 102 in step (c) is not greater than the moving speed of the mobile platform 102 in step (a). Thus, the moving speed of the mobile platform 102 in step (c) may also eliminate or partially eliminate the position deviation caused by the moving speed of the mobile platform 102 in step (a).

Considering the deviation caused by the detection precision of the limit switch and the moving speed during mechanical positioning is beneficial for precise positioning. The positioning method comprises steps (a)-(c) to eliminate or reduce the influence of the detection precision of the limit switch and the moving speed of the mobile platform 102 in these steps on precise positioning.

The moving speed of the mobile platform 102 in step (d) is not greater than a second preset value, and the second preset value is related to an allowable error of positioning. In some examples, the reaction device 200 is provided with one or more channels 21, the positioning is for enabling fields of view acquired by the imaging assembly 110 to be from the channels, the allowable error of the positioning is related to the width of the channel, and the width of the channel is defined as the length of the channel 21 in the first direction.

Specifically, in order to enable the optical axis OP and the starting position of the reaction device 200 to satisfy a preset relationship, such as a perpendicular relationship, the second preset value is used as the upper limit of the moving speed of the mobile platform 102 in step (d), and this limit can enable the positioning deviation caused by the moving speed of the mobile platform 102 in step (d) to be within the allowable error range of the positioning.

In this embodiment, when positioning a batch of reaction devices 200 with the same specification and dimension, only any one of the reaction devices 200 placed on the mobile platform 102 needs to be subjected to channel positioning After the positioning is completed, the coordinates are recorded and saved. When a reaction device 200 with the same specification and dimension is used, the mobile platform 102 can be directly used to move the reaction device 200 to the saved coordinate position to realize the initial positioning, which can save a lot of time for sequence determination. In some examples, the mechanical tolerance among the reaction devices 200 with the same specification and dimension is 0.1 mm.

In one example, the positioning method is to achieve precise positioning of a target position. The target position is, for example, any field of view in a certain channel on the reaction device 200. The width of the channel is 1.8 mm, and the allowable error of the positioning is ±0.9 mm, such that the imaging assembly 110 can acquire images of the target position. The tolerance among the reaction devices 200 with the same specification and that of the related mechanical structure are ±0.2 mm. Therefore, it will be appreciated that the allowable deviation of the entire movement process shall not exceed ±0.7 mm if the positioning of the target position is to be achieved.

In certain embodiments, the positioning is for enabling fields of view acquired by the imaging assembly 110 to be from a designated channel on the reaction device 200, and the second preset value is related to the width of the designated channel. In this way, the imaging assembly 110 can acquire images of the designated channel of the reaction device 200.

In the above example, the designated channel may be a first channel 24 of the reaction device 200. More specifically, a left end position 26 of the first channel 24 may be used as the starting position of photographing for the imaging assembly 110. Photographing positions 28 comprising the starting position 26 may be used as fields of view (FOVs) of the imaging assembly 110.

In some examples, a preset distance is a distance, on the stroke, between the first limit and the position of the mobile platform 102 when the preset relationship is satisfied. In this way, by moving from the first limit by the preset distance in step (d), the optical axis OP and the position of the reaction device 200 can satisfy the preset relationship.

Specifically, in the example described above, the optical axis OP and the first channel 24 of the reaction device 200 can satisfy a perpendicular relationship. The preset distance can be measured in advance before moving the mobile platform 102, and recorded and saved for use when needed.

It should be noted that in the coordinate system shown in the figure, the position of the mobile platform 102 can be obtained by an inquiry board card, and the inquiry board card can provide the coordinate values according to the number of steps of the movement of the motor that drives the mobile platform 102 to move. In an example, the frequency of the inquiry board card to calculate and output coordinate values is 20 ms.

In certain embodiments, the positioning method comprises: prompting information of success when the optical axis OP and the position of the reaction device 200 satisfy a preset relationship. In this way, when the positioning of the reaction device 200 is successful, the user can continue subsequent operations in time, which improves the efficiency of sequence determination.

Specifically, the information of success can be prompted by sound and/or light. For example, the sequencing system 300 comprises a speaker and/or a display screen, and when the optical axis OP and the position of the reaction device 200 satisfy the preset relationship, the speaker can play the information of success, and the display screen can display the information of success, etc. Of course, the sequencing system 300 may also comprise a vibrating element. When the optical axis OP and the position of the reaction device 200 satisfy the preset relationship, the vibrating element vibrates to prompt the information of success.

Figure 6:
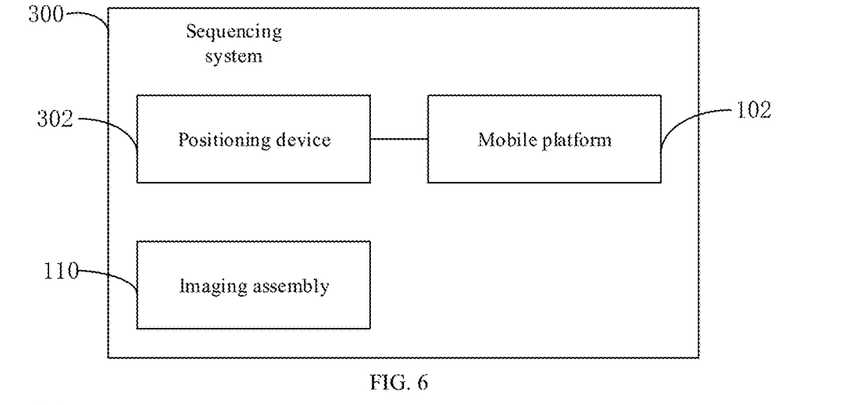
FIG. 6 is a schematic diagram of a module of a sequencing system according to an embodiment of the present disclosure.

Referring to FIG. 2 and FIG. 6, an embodiment of the present disclosure provides a sequencing system 300. The sequencing system 300 comprises a positioning device 302, an imaging assembly 110 and a mobile platform 102; the imaging assembly 110 comprises an optical axis OP, and the mobile platform 102 bears a reaction device 200; the imaging assembly 110 is located above the reaction device 200, a limit switch is configured for controlling stroke of the mobile platform 102 in a first direction, and the stroke comprises a first limit; the positioning device 302 is configured for:

(a) moving the mobile platform 102 in a direction approaching the first limit at a first step space until a distance between a current position of the reaction device 200 and a previous position of the reaction device 200 is smaller than the first step space;

(b) moving the mobile platform 102 in a direction away from the first limit;

(c) moving the mobile platform 102 in a direction approaching the first limit until the mobile platform 102 reaches the first limit; and (d) moving the mobile platform 102 in the direction away from the first limit for a preset distance such that the optical axis OP and the position of the reaction device 200 satisfy a preset relationship.

The sequencing system 300 described above, by the positioning device 302 comprised therein, enables the mobile platform 102 to move back and forth in the first direction. Thus, in combination with setting a moving speed/a moving step space, rapid and precise positioning can be realized, such that the optical axis of the imaging assembly 110 and the position of the reaction device 200 satisfy the preset relationship, and thereby subsequently the imaging assembly 110 can continuously photograph to give information of all target fields of view in a predetermined area.

It should be noted that the explanation and description of the technical features and benefits of the positioning method in any of the aforementioned embodiments and examples are also applicable to the sequencing system 300 according to the present embodiment. There will be no detailed description herein to avoid redundancy.

In certain embodiments, the moving speed of the mobile platform in step (c) is not greater than a first preset value, and the first preset value is related to an allowable error of positioning.

In certain embodiments, the moving speed of the mobile platform in step (c) is not greater than the moving speed of the mobile platform in step (a).

In certain embodiments, a minimum distance the mobile platform needs to move in step (b) is related to the moving speed of the mobile platform in step (a).

In certain embodiments, the moving speed of the mobile platform in step (d) is not greater than a second preset value, and the second preset value is related to an allowable error of positioning.

In certain embodiments, the reaction device is provided with one or more channels, the allowable error of the positioning is related to the width of the channel, and the width of the channel is defined as the length of the channel in the first direction.

In certain embodiments, the positioning device is configured for prompting information of success when the optical axis and the position of the reaction device satisfy a preset relationship.

Figure 7:
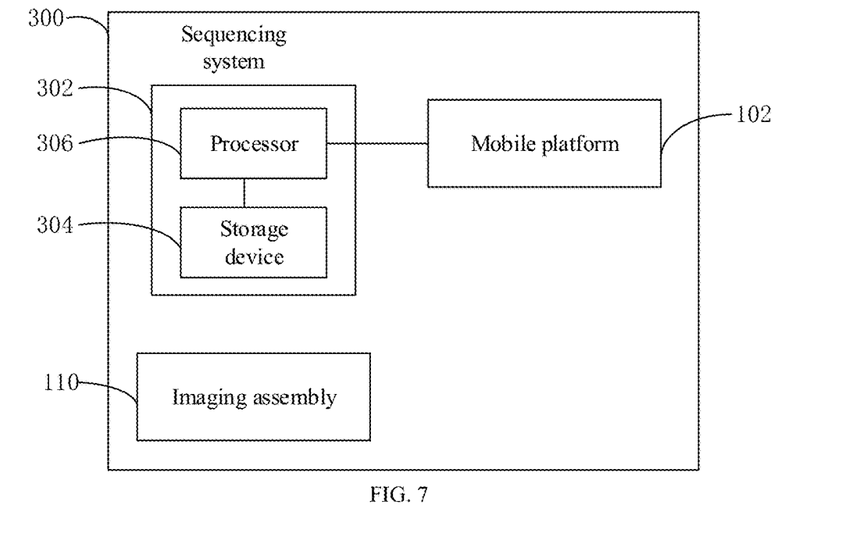
FIG. 7 is a schematic diagram of another block of a sequencing system according to an embodiment of the present disclosure.

Referring to FIG. 7, an embodiment of the present disclosure provides a positioning device 302 for a sequencing system 300. The sequencing system 300 comprises an imaging assembly 110 and a mobile platform 102; the imaging assembly 110 comprises an optical axis OP, and the mobile platform 102 bears a reaction device 200; the imaging assembly 110 is located above the reaction device 200, a limit switch is configured for controlling stroke of the mobile platform 102 in a first direction, and the stroke comprises a first limit. The positioning device 302 comprises a storage device 304 and a processor 306; the storage device is configured for storing data that comprises a computer-executable program, and the processor is configured for executing the computer-executable program, wherein executing the computer-executable program comprises performing the steps of the positioning method of any one of the embodiments described above.

In addition, the sequencing system 300 shown in FIG. 7 comprises the positioning device 302.

An embodiment of the present disclosure provides a computer-readable storage medium configured for storing a program that, when executed by a computer, causes the computer to perform the method according to any one of the embodiments described above. The computer-readable storage medium may include: read-only memory, random access memory, magnetic disk, optical disk, or the like.

In the description of this specification, the description with reference to the terms "one embodiment", "certain embodiments", "exemplary embodiments", "example", "specific example", or "some examples" means that the specific features, structures, materials or characteristics described in combination with the embodiments or examples are included in at least one embodiment or example of the present disclosure. In this specification, the schematic description of the aforementioned terms do not necessarily refer to the same embodiment or example. Moreover, the particular features, structures, materials or characteristics described may be combined in any one or more embodiments or examples in any appropriate manner.

Logic and/or steps shown in the flowcharts or otherwise described herein, for example, may be considered as a sequencing list of executable instructions that are used to implement logical functions, and may be specifically implemented in any computer-readable storage medium for use by an instruction execution system, device, or apparatus (for example, a computer-based system, a system including a processor, or another system that can get instructions from the instruction execution system, device, or apparatus and execute the instructions), or for use in combination with the instruction execution system, device or apparatus. As used herein, the "computer-readable storage medium" may be any device that may include, store, communicate, propagate, or transmit a program for use by an instruction execution system, device, or apparatus, or for use in combination with the instruction execution system, device, or apparatus.

In addition, each functional unit in each embodiment of the present disclosure may be integrated in one processing module, or each unit may physically exist alone, or two or more than two units may be integrated in one module. The above-mentioned integrated module may be implemented in the form of hardware or in the form of a software functional module. The integrated module may also be stored in a computer-readable storage medium if it is implemented in the form of a software functional module and is sold or used as standalone products.

Although the embodiments of the present disclosure have been shown and described above, it will be appreciated that the aforementioned embodiments are exemplary and are not to be construed as limiting the present disclosure, and that those of ordinary skill in the art may make changes, modifications, replacements and variations to such embodiments without departing from the scope of the present disclosure.

What is claimed is:

1. A positioning method for a sequencing system, wherein the sequencing system comprises an imaging assembly, a mobile platform, and a positioning device, the imaging assembly comprises an optical axis, the mobile platform bears a reaction device, the imaging assembly is located above the reaction device, a limit switch is configured for controlling a stroke of the mobile platform in a first direction, and the stroke comprises a first limit, the positioning device performing the method comprising:
   (a) moving the mobile platform in a direction approaching the first limit at a first step space until a distance between a current position of the reaction device and a previous position of the reaction device is smaller than the first step space;
   (b) moving the mobile platform in a direction opposite to the moving direction in (a);
   (c) moving the mobile platform in the moving direction in (a) until the mobile platform reaches the first limit; and
   (d) moving the mobile platform in the direction opposite to the moving direction in (a) for a preset distance such that the optical axis and the position of the reaction device satisfy a preset relationship.

2. The method according to claim 1, wherein a moving speed of the mobile platform in step (c) is not greater than a first preset value, and the first preset value is related to an allowable error of the positioning.

3. The method according to claim 1, wherein a moving speed of the mobile platform in step (c) is not greater than a moving speed of the mobile platform in step (a).

4. The method according to claim 1, wherein a minimum distance the mobile platform needs to move in step (b) is related to a moving speed of the mobile platform in step (a).

5. The method according to claim 1, wherein a moving speed of the mobile platform in step (d) is not greater than a second preset value, and the second preset value is related to an allowable error of the positioning.

6. The method according to claim 2, wherein the reaction device is provided with one or more channels, the positioning is for enabling fields of view acquired by the imaging assembly to be from the one or more channels, the allowable error of the positioning is related to the width of a first channel of the one or more channels, and the width of each channel is defined as the length of each channel in the first direction.

7. The method according to claim 1, wherein the method further comprises: prompting information of success when the optical axis and the position of the reaction device satisfy the preset relationship.

8. The method according to claim 2, wherein the moving speed of the mobile platform in step (c) is not greater than a moving speed of the mobile platform in step (a).

9. The method according to claim 2, wherein a moving speed of the mobile platform in step (d) is not greater than a second preset value, and the second preset value is related to the allowable error of the positioning.

10. The method according to claim 5, wherein the reaction device is provided with one or more channels, the positioning is for enabling fields of view acquired by the imaging assembly to be from the one or more channels, the allowable error of the positioning is related to the width of a first channel of the one or more channels, and the width of each channel is defined as the length of each channel in the first direction.

11. A sequencing system, comprising a positioning device, an imaging assembly and a mobile platform, wherein the imaging assembly comprises an optical axis, the mobile platform bears a reaction device, the imaging assembly is located above the reaction device, a limit switch is configured for controlling a stroke of the mobile platform in a first direction, the stroke comprises a first limit, and the positioning device is configured for:
   (a) moving the mobile platform in a direction approaching the first limit at a first step space until a distance between a current position of the reaction device and a previous position of the reaction device is smaller than the first step space;
   (b) moving the mobile platform in a direction away from the first limit;
   (c) moving the mobile platform in a direction approaching the first limit until the mobile platform reaches the first limit; and
   (d) moving the mobile platform in the direction away from the first limit for a preset distance such that the optical axis and the position of the reaction device satisfy a preset relationship.

12. The system according to claim 11, wherein a moving speed of the mobile platform in step (c) is not greater than a first preset value, and the first preset value is related to an allowable error of the positioning.

13. The system according to claim 11 or 12, wherein the moving speed of the mobile platform in step (c) is not greater than a moving speed of the mobile platform in step (a).

14. The system according to claim 11, wherein a minimum distance the mobile platform needs to move in step (b) is related to the moving speed of the mobile platform in step (a).

15. The system according to claim 11, wherein a moving speed of the mobile platform in step (d) is not greater than a second preset value, and the second preset value is related to an allowable error of the positioning.

16. The system according to claim 15, wherein the reaction device is provided with one or more channels, the allowable error of the positioning is related to the width of a first channel of the one or more channels, and the width of each channel is defined as the length of each channel in the first direction.

17. The system according to claim 16, wherein the positioning device is further configured for prompting information of success when the optical axis and the position of the reaction device satisfy the preset relationship.

18. A sequencing system, comprising a positioning device, an imaging assembly and a mobile platform, wherein the imaging assembly comprises an optical axis, the mobile platform bears a reaction device, the imaging assembly is located above the reaction device, a limit switch is configured for controlling a stroke of the mobile platform in a direction, the stroke comprises a first limit, and the positioning device comprises:

a storage device configured for storing data, wherein the data comprises a computer-executable program; and a processor configured to execute the computer-executable program which causes the positioning device to perform actions comprising:

moving the mobile platform in a first direction approaching the first limit at a first step space until a distance between a current position of the reaction device and a previous position of the reaction device is smaller than the first step space;

moving the mobile platform in a second direction opposite to the first direction;

moving the mobile platform in the first direction until the mobile platform reaches the first limit; and moving the mobile platform in the second direction for a preset distance such that the optical axis and the position of the reaction device satisfy a preset relationship.

19. The sequencing system according to claim 18, wherein a moving speed of the mobile platform when moving in the first direction until the mobile platform reaches the first limit is not greater than a first preset value, and the first preset value is related to an allowable error of the positioning.

20. The sequencing system according to claim 19, wherein the reaction device is provided with one or more channels, the positioning is for enabling fields of view acquired by the imaging assembly to be from the one or more channels, the allowable error of the positioning is related to the width of a first channel of the one or more channels, and the width of each channel is defined as the length of each channel in the first direction.

* * * * *

UNITED STATES PATENT AND TRADEMARK OFFICE
CERTIFICATE OF CORRECTION

| | | |
|---|---|---|
| PATENT NO. | : 11,421,272 B2 | Page 1 of 1 |
| APPLICATION NO. | : 17/417035 | |
| DATED | : August 23, 2022 | |
| INVENTOR(S) | : Sun et al. | |

It is certified that error appears in the above-identified patent and that said Letters Patent is hereby corrected as shown below:

In the Claims

Column 12, Claim 13, Line 64:
"The system according to claim 11 or 12," should read: --The system according to claim 12,--.

Signed and Sealed this
Thirty-first Day of December, 2024

Derrick Brent
*Acting Director of the United States Patent and Trademark Office*